(12) United States Patent
Saika

(10) Patent No.: US 11,089,956 B2
(45) Date of Patent: Aug. 17, 2021

(54) OPHTHALMOLOGIC APPARATUS AND METHOD OF CONTROLLING THE SAME

(71) Applicant: TOPCON CORPORATION, Tokyo (JP)

(72) Inventor: Makoto Saika, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 433 days.

(21) Appl. No.: 16/129,839

(22) Filed: Sep. 13, 2018

(65) Prior Publication Data

US 2019/0082955 A1 Mar. 21, 2019

(30) Foreign Application Priority Data

Sep. 20, 2017 (JP) .............................. JP2017-180549

(51) Int. Cl.
| | | |
|---|---|---|
| *A61B 3/117* | (2006.01) | |
| *A61B 3/113* | (2006.01) | |
| *A61B 3/00* | (2006.01) | |
| *A61B 3/14* | (2006.01) | |
| *A61B 3/107* | (2006.01) | |
| *A61B 3/11* | (2006.01) | |

(Continued)

(52) U.S. Cl.
CPC ............ *A61B 3/117* (2013.01); *A61B 3/0025* (2013.01); *A61B 3/102* (2013.01); *A61B 3/107* (2013.01); *A61B 3/112* (2013.01); *A61B 3/113* (2013.01); *A61B 3/12* (2013.01); *A61B 3/14* (2013.01)

(58) Field of Classification Search
CPC ....... A61B 3/117; A61B 3/113; A61B 3/0025; A61B 3/14; A61B 3/107; A61B 3/112; A61B 3/12; A61B 3/102
See application file for complete search history.

(56) References Cited

U.S. PATENT DOCUMENTS

| | | |
|---|---|---|
| 5,491,524 A | 2/1996 | Hellmuth et al. |
| 2006/0187462 A1* | 8/2006 | Srinivasan ............. A61B 3/102 |
| | | 356/479 |

(Continued)

FOREIGN PATENT DOCUMENTS

| | | |
|---|---|---|
| JP | 2009-142313 A | 7/2009 |
| JP | 2014-500096 A | 1/2014 |

(Continued)

OTHER PUBLICATIONS

Extended Search Report issued in European Application 18194497.6-1124 dated Feb. 14, 2019.

*Primary Examiner* — Darryl J Collins
*Assistant Examiner* — Matthew Y Lee
(74) *Attorney, Agent, or Firm* — Xsensus LLP

(57) ABSTRACT

An ophthalmologic apparatus is configured to control an optical scanner so as to perform a scan by measurement light in an intersecting direction which intersects a traveling direction of the measurement light, to specify a scan length based on a detection result of interference light corresponding to the scan, the detection result being acquired by an interference optical system, the scan length being a length of a scan range in the intersecting direction within a characteristic region in an anterior segment of the subject's eye, and to specify a movement amount of the subject's eye based on a reference value of the characteristic region and the scan length.

13 Claims, 14 Drawing Sheets

(51) Int. Cl.
*A61B 3/12* (2006.01)
*A61B 3/10* (2006.01)

(56) References Cited

U.S. PATENT DOCUMENTS

| | | |
|---|---|---|
| 2008/0055543 A1* | 3/2008 | Meyer .................... A61B 3/113 |
| | | 351/205 |
| 2009/0149742 A1 | 6/2009 | Kato et al. |
| 2012/0140174 A1 | 6/2012 | Hee et al. |
| 2014/0049753 A1 | 2/2014 | Bajramovic et al. |
| 2015/0245765 A1 | 9/2015 | Fujii et al. |

FOREIGN PATENT DOCUMENTS

| | | |
|---|---|---|
| JP | 2015-160103 A | 9/2015 |
| JP | 2015-181789 A | 10/2015 |

* cited by examiner

OPHTHALMOLOGIC APPARATUS AND METHOD OF CONTROLLING THE SAME

CROSS-REFERENCE TO RELATED APPLICATION

This application is based upon and claims the benefit of priority from Japanese Patent Application No. 2017-180549, filed Sep. 20, 2017; the entire contents of which are incorporated herein by reference.

FIELD

Embodiments according to present invention relate to an ophthalmologic apparatus that optically examines a subject's eye and a method of controlling the same.

BACKGROUND

In recent years, attention has been drawn to optical coherence tomography (OCT) which is used to measure or image the morphology of an object to be measured using light beams emitted from a laser light source or the like. Unlike X-ray computed tomography (CT), OCT is not invasive on the human body, and therefore is expected to be applied to the medical field and the biological field, in particular. For example, in the ophthalmological field, apparatuses for forming images of the fundus, the cornea, or the like have been in practical use. Such an apparatus using OCT (OCT apparatus) can be used to observe a variety of sites (fundus or anterior segment) of a subject's eye. In addition, because of the ability to acquire high precision images, the OCT apparatuses are applied to the diagnosis of various eye diseases.

For example, Japanese Unexamined Patent Application Publication No. 2015-160103 discloses an ophthalmologic apparatus capable of observing the anterior segment of the subject's eye. According to such the ophthalmologic apparatus, a cross-sectional shape of the anterior segment can be specified by scanning the anterior segment, and information on the shape of the front and back surfaces of the cornea, the thickness of the cornea, the anterior chamber depth, or the like can be acquired. Furthermore, two-dimensional or three-dimensional distribution of the corneal shape, the corneal thickness, the anterior chamber depth, or the like for the anterior segment can be obtained by analyzing a plurality of cross-sectional shapes.

As a method of scanning the anterior segment, radial scan, in which a plurality of scans are performed radially around the pupil of the subject's eye, is known. However, when the subject's eye moves due to the involuntary eye movement, line-of-sight deviation, or the like during scanning, accurate information can not be acquired. In case of scanning the fundus, a method of specifying a movement amount and a movement direction of the fundus due to the involuntary eye movement or the like with reference to a characteristic position in a front image of the fundus, and canceling displacement of a scan position according to the specified movement amount and the like (that is, tracking) is known. However, in case of scanning the anterior segment, characteristic positions are absent in the anterior segment, thereby it is difficult to adopt tracking as in the case of scanning the fundus.

Therefore, various methods for suitably maintaining scan position in scanning the anterior segment have been proposed.

For example, Japanese Unexamined Patent Application Publication No. 2009-142313 discloses a method of acquiring an anterior segment image of the subject's eye, specifying a corneal apex position from the acquired anterior segment image, and performing position matching with reference to the specified corneal apex position.

Further, for example, Japanese Unexamined Patent Application Publication No. 2015-181789 discloses a method of monitoring a movement of the subject's eye by perform scan (movement amount measurement scan) for a position across a characteristic position, which is different from a scan (imaging scan) for an evaluation position (in particular, see paragraph 0314 and FIG. 22).

Further, for example, Japanese Unexamined Patent Application Publication (Translation of PCT Application) No. 2014-500096 discloses a method of scanning the anterior segment using scan pattern combing radial scan and circle scan (in particular, see paragraphs 0060 to 0062).

SUMMARY

The first aspect of the embodiments is an ophthalmologic apparatus including: an optical scanner; an interference optical system that splits light from a light source into measurement light and reference light, projects the measurement light onto a subject's eye via the optical scanner, and detects interference light generated from returning light of the measurement light from the subject's eye and the reference light; a controller that controls the optical scanner so as to perform scan by the measurement light in an intersecting direction which intersects a traveling direction of the measurement light; and an analyzer that specifies a scan length based on a detection result of the interference light corresponding to the scan, the detection result being acquired by the interference optical system, the scan length being a length of a scan range in the intersecting direction within a characteristic region in an anterior segment of the subject's eye, and specifies a movement amount of the subject's eye based on a reference value of the characteristic region and the scan length.

Further, in the second aspect of the embodiments, in the first aspect, the analyzer may specify a movement direction of the subject's eye based on a position of the scan range within the characteristic region in an entire scan range of the scan.

Further, in the third aspect of the embodiments, in the second aspect, the controller may control the optical scanner to start radial scan in which a plurality of scans including the scan in the intersecting direction are performed radially around a scan center position, when the scan center position substantially coincides with a reference position within the characteristic region in a plane intersecting the traveling direction.

Further, in the fourth aspect of the embodiments, in the third aspect, the analyzer may include a property distribution calculator that obtains a distribution of property information of the anterior segment by means of a detection result of the interference light in which positional displacement with respect to the reference position is corrected based on the movement amount and the movement direction.

Further, in the fifth aspect of the embodiments, in the fourth aspect, the property information may include at least one of corneal shape information, corneal thickness information, and anterior chamber depth information.

Further, the sixth aspect of the embodiments, in any one of the third to the fifth aspects, further may include a movement mechanism that moves the subject's eye and the interference optical system relative to each other, wherein the reference position is a registration reference position of the interference optical system with respect to the subject's eye.

Further, in the seventh aspect of the embodiments, in any one of the third to the sixth aspects, the reference position may be a pupil center position, a pupil barycentric position, a corneal center position, a corneal apex position, or a center position of the subject's eye.

Further, in the eighth aspect of the embodiments, in any one of the third to the seventh aspects, the reference value may be a value corresponding to a pupil diameter, an iris outer diameter, or a distance between corner angles obtained by performing scan which passes through the reference position.

Further, the ninth aspect of the embodiments, in any one of the first to the eighth aspects, further may include an anterior segment imaging system for imaging the anterior segment, wherein the analyzer may include a first specifying unit that specifies the reference value in the characteristic region by analyzing an anterior segment image acquired by using the anterior segment imaging system.

Further, the tenth aspect of the embodiments, in any one of the first to the ninth aspects, further may include an image forming unit that forms a tomographic image of the anterior segment based on the detection result of the interference light, wherein the analyzer may include a second specifying unit that specifies the scan length by analyzing the tomographic image.

Further, the eleventh aspect of the embodiments, is a method of controlling an ophthalmologic apparatus that scans an anterior segment of a subject's eye by using optical coherence tomography, the method including; a projection step that splits light from a light source into measurement light and reference light and projects the measurement light onto a subject's eye via an optical scanner; a control step that controls the optical scanner so as to perform scan by the measurement light in an intersecting direction which intersects a traveling direction of the measurement light incident on the anterior segment; an interference light detection step that detects interference light generated from returning light of the measurement light from the subject's eye and the reference light; and a movement amount specifying step that specifies a scan length based on a detection result of the interference light corresponding to the scan, the scan length being a length of a scan range in the intersecting direction within a characteristic region in the anterior segment, and specifies a movement amount of the subject's eye based on a reference value of the characteristic region and the scan length.

Further, the twelfth aspect of the embodiments, in the eleventh aspect, may include a movement direction specifying step that specifies a movement direction of the subject's eye based on a position of the scan range within the characteristic region in an entire scan range of the scan.

Further, the thirteenth aspect of the embodiments, in the eleventh or the twelfth aspect, in the control step, radial scan in which a plurality of scans including the scan in the intersecting direction may be performed radially around a scan center position is started, when the scan center position substantially coincides with a reference position within the characteristic region in a plane intersecting the traveling direction.

The various features of the above aspects may be variously combined with some features included and others excluded to suit a variety of different applications.

DETAILED DESCRIPTION

Figure 1:
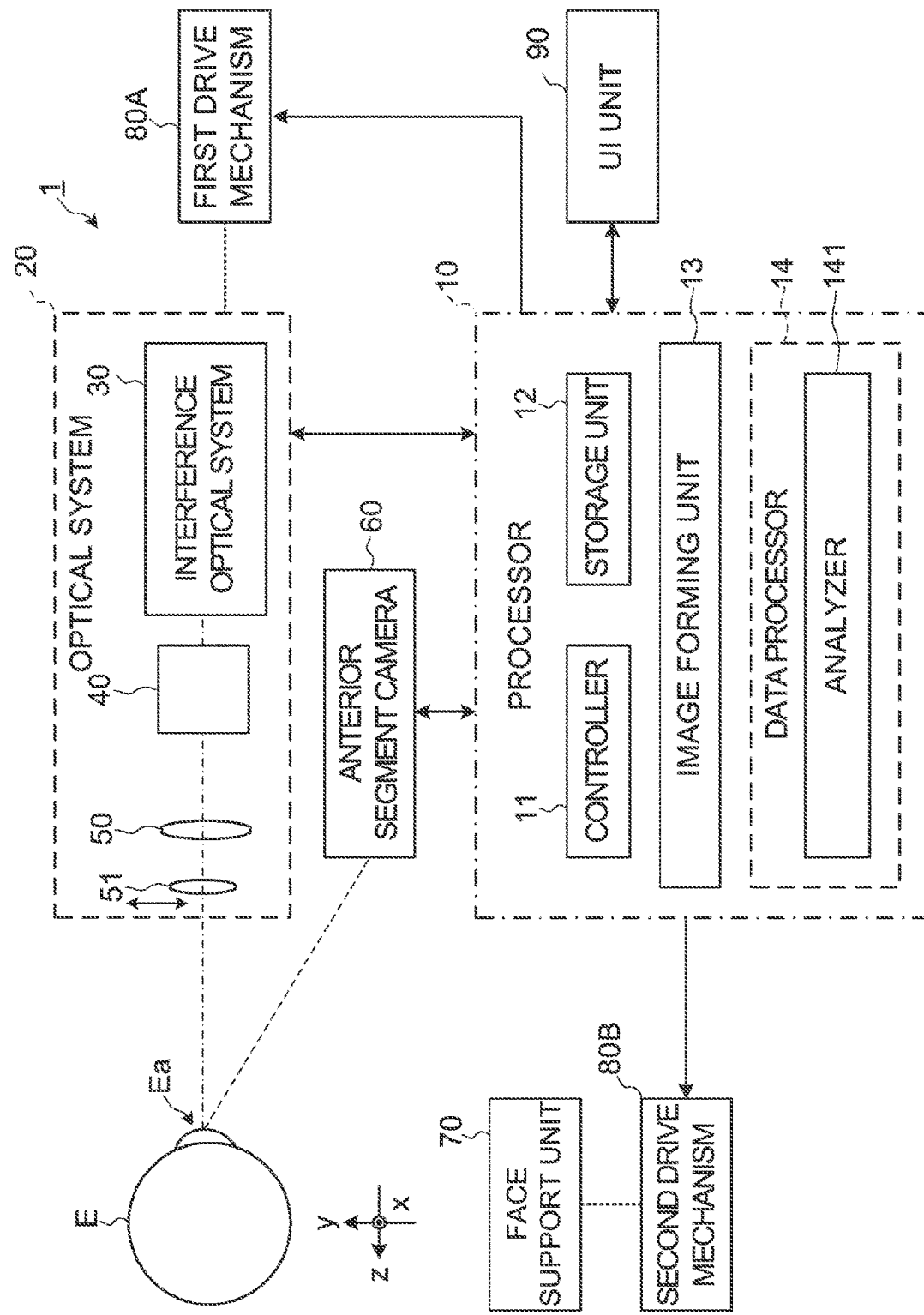
FIG. 1 is a schematic diagram showing an example of the configuration of an ophthalmologic apparatus according to embodiments.

In the conventional technique, the scan timing of the anterior segment is different from the acquiring timing of images of the anterior segment. Therefore, due to the difference between the scan timing and the acquiring timing of the image, a movement of the subject's eye specified by using the acquired image does not coincide with a displacement of the scan position. Thereby, it is not possible to correct the scan position to an appropriate position.

Further, when the optical system moves, it is difficult for the movement of the optical system to follow the involuntary eye movement or the like, and vibration caused by the movement of the optical system may also occur. Furthermore, if the displacement of the scan position due to the involuntary eye movement or the like during scanning is corrected only by the scan pattern, the scan time becomes longer, and it may lead to the movement of the subject's eye during scanning.

According to some embodiments of the present invention, the ophthalmologic apparatus and the method of controlling the same capable of acquiring data of the subject's eye with accuracy even when the movement of the subject's eye occurs during scanning can be provided.

Referring now to the drawings, exemplary embodiments of an ophthalmologic apparatus and a method of controlling the same according to the present invention are described below. The ophthalmologic apparatuses according to the present invention are used for optical examinations of the subject's eye. Such ophthalmologic apparatuses include ophthalmologic imaging apparatuses and ophthalmologic measuring apparatuses. Examples of ophthalmologic imaging apparatuses include an OCT apparatus, a fundus camera, a scanning laser ophthalmoscope, a slit lamp microscope, and the like. Examples of ophthalmologic measuring apparatuses include an eye refractivity examination apparatus, a tonometer, a specular microscope, a wave-front analyzer, and the like. Cases of applying the present invention to an OCT apparatus are explained in the following embodiments; however, the present invention may be applied to any other types of ophthalmologic apparatuses.

In this specification, an image obtained by optical coherence tomography is sometimes referred to as an OCT image. Furthermore, a measuring action for forming an OCT image is sometimes referred to as an OCT measurement. It should be noted that the contents of the documents cited in this specification may be employed in the following embodiments.

In the following embodiments, an OCT apparatus using OCT of so-called spectral domain type, in which a low-coherence light source and a spectrometer are included, is described. However, the present invention may also be applied to OCT apparatuses using other types than spectral domain, such as swept source type and en-face type. Note that the swept source OCT is a modality of imaging the morphology of an object to be measured by: scanning (sweeping) the wavelength of light that is irradiated to the object to be measured; acquiring the spectral intensity distribution by successively detecting interference light obtained from superposing the reflected light of the light of each wavelength on reference light; and performing Fourier transform on the acquired spectral intensity distribution. The en-face OCT is a method of irradiating light with a predetermined beam diameter to an object to be measured and analyzing the components of interference light obtained from superposing the reflected light thereof and reference light, thereby forming an image of a cross-section of the object to be measured orthogonal to the traveling direction of the light, and it is also referred to as full-field type.

The ophthalmologic apparatus to the embodiments is capable of switching applications for measuring a fundus to for measuring an anterior segment, by inserting an optical element such as a front lens or the like at a predetermined position of the optical system. The measurement target sites are not limited to the fundus and the anterior segment. The measurement target site may be an arbitrary site of the subject's eye such as a vitreous body or a crystalline lens. Furthermore, it is also possible to prepare optical elements corresponding to the measurement target sites and selectively apply these optical elements to the ophthalmologic apparatus. It is also possible to automatically select use/non-use of the optical element such as the front lens or the like and/or select the optical element to be applied. These selection processes are performed based on the contents of photographing performed in the past, the name of injuries and diseases, or the like, for example.

Hereinafter, the direction of the optical axis of the optical system of the apparatus is defined as z direction (front-back direction), the horizontal direction perpendicular to the optical axis of the optical system of the apparatus is defined as x direction (horizontal direction), and the vertical direction perpendicular to the optical axis of the optical system of the apparatus is defined as y direction (vertical direction).

[Configuration]

Figure 2:
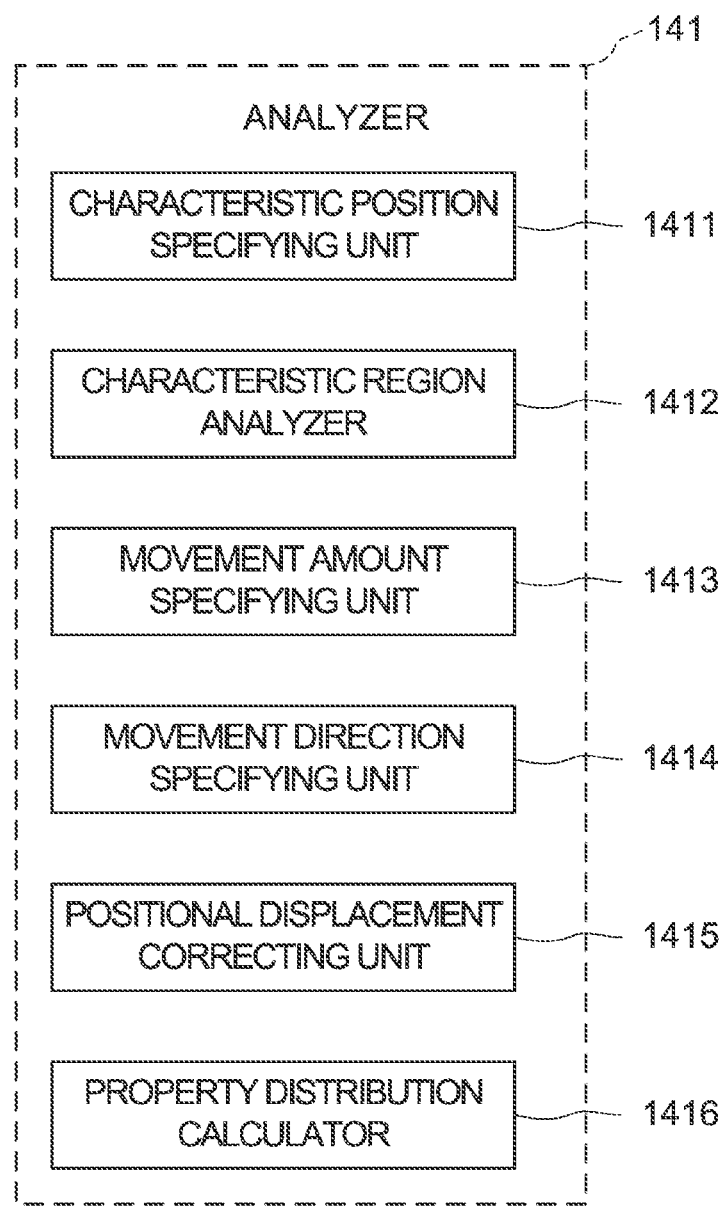
FIG. 2 is a schematic diagram showing an example of the configuration of the ophthalmologic apparatus according to the embodiments.

FIG. 1 and FIG. 2 show an exemplary configuration of the ophthalmologic apparatus according to the embodiments. An ophthalmologic apparatus 1 according to the embodiments has the functions of acquiring data of the subject's eye E, i.e., at least one of the function of imaging a subject's eye E and the function of measuring the properties of the subject's eye E.

The ophthalmologic apparatus 1 includes a processor 10, an optical system 20, anterior segment cameras 60, a face support unit 70, a first drive mechanism 80A, a second drive mechanism 80B, and a user interface (UI) unit 90. The anterior segment cameras 60 may be included in the optical system 20. It should be noted that the ophthalmologic apparatus 1 may be provided with only one of the first drive mechanism 80A and the second drive mechanism 80B.

The optical system 20 includes an interference optical system 30, an optical scanner 40, an objective lens 50, and a front lens 51. The front lens 51 is configured to be capable of inserting and being removed from between the subject's eye E and the objective lens 50. Two or more of the anterior segment cameras 60 are provided at positions at which the subject's eye E is viewed from different angles with respect to the optical axis of the objective lens 50.

(Processor 10)

The processor 10 performs various types of information processing. The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA).

For example, the processor 10 reads a program stored in a memory circuit or a storage device and executes it, thereby implementing the functions according to the embodiments. At least a part of the memory circuit or the storage device may be included in the processor 10. In addition, at least a part of the memory circuit or the storage device may be provided outside of the processor 10. Processes that can be performed by the processor 10 are described later. The processor 10 includes a controller 11, a storage unit 12, an image forming unit 13, and a data processor 14.

(Controller 11)

The controller 11 controls each unit of the ophthalmologic apparatus 1. In particular, the controller 11 controls the optical system 20, the first drive mechanism 80A, and the second drive mechanism 80B.

The control of the optical system 20 includes the control for performing OCT measurement by the interference optical system 30. In order to perform OCT measurement, the controller 11 can control the optical scanner 40 so that the projection position of a measurement light in the subject's eye E moves according to a predetermined scan pattern. Examples of scan patterns include three-dimensional scan, radial scan, line scan, circle scan, and the like.

Furthermore, the controller 11 can control the position matching (alignment) of the optical system 20 with respect to the subject's eye E. In case of manual alignment, upon receiving an operation on the user interface unit 90 by the user, the controller 11 controls at least one of the first drive mechanism 80A and the second drive mechanism 80B to move the optical system 20 and the subject's eye E relative to each other. In case of auto alignment, the controller 11 controls at least one of the first drive mechanism 80A and the second drive mechanism 80B based on the relative position between the optical system 20 and the subject's eye E to move the optical system 20 and the subject's eye E relative to each other. The controller 11 can relatively move the optical system 20 and the subject's eye E based on the relative position with the subject's eye E acquired from the images of the anterior segment cameras 60. Control operations that can be performed by the controller 11 are described later.

(Storage Unit 12)

The storage unit 12 stores various types of data. Examples of the data stored in the storage unit 12 include data (measurement data, detection result of an interference light, etc.) acquired by the interference optical system 30 and information related to the subject and the subject's eye. The storage unit 12 may store a variety of computer programs and data for the operation of the ophthalmologic apparatus 1. The storage unit 12 stores various types of data that is used and referred to in the processes described later. The storage unit 12 includes the memory circuit and the storage device described above.

(Image Forming Unit 13)

The image forming unit 13 forms image data of a tomographic image, a two-dimensional image, a three-dimensional image, and the like of the subject's eye based on a detection result (described after) of the interference light acquired by the interference optical system 30. As with a conventional spectral domain OCT, this process includes noise removal (noise reduction), filtering, fast Fourier transform (FFT), and the like. In the case of another type of OCT apparatus, the image forming unit 13 performs known processes according to the type thereof.

(Data Processor 14)

The data processor 14 performs various types of data processing. In particular, the data processor 14 analyzes the detection result of the interference light acquired by the interference optical system 30, the image of the subject's eye formed by the image forming unit 13, and the images acquired by the anterior segment cameras 60. The image processor 14 is provided with an analyzer 141. As shown in FIG. 2, the analyzer 141 includes a characteristic position specifying unit 1411, a characteristic region analyzer 1412, a movement amount specifying unit 1413, a movement direction specifying unit 1414, a positional displacement correcting unit 1415, and a property distribution calculator 1416. Their operations are described later.

(Optical System 20)

In addition to the configuration illustrated in FIG. 1, the optical system 20 may be provided with an optical system (observation optical system, imaging optical system, etc.) for photographing the subject's eye E from the front, or an alignment optical system. Besides, the optical system 20 may also be provided with a configuration for focusing of the interference optical system 30 and the like. Furthermore, the optical system 20 may be further provided with a light source (anterior segment illumination light source) for illuminating the anterior segment Ea of the subject's eye E.

(Interference Optical System 30)

The interference optical system 30 includes an optical system for acquiring OCT images of the fundus or the anterior segment of the subject's eye E. The optical system has a similar configuration to a conventional spectral-domain-type OCT apparatus. That is to say, the optical system is configured to split light (e.g. low-coherence light) from a light source into reference light and measurement light, make the measurement light propagated through the fundus or the anterior segment and the reference light propagated through a reference optical path interfere with each other to generate the interference light, and detect the spectral component of this interference light. The detection result (detection signal) is sent to the processor 10.

When this optical system has a configuration similar to that of swept source type OCT apparatuses, the ophthalmologic apparatus can include a wavelength tunable light source in place of the light source that outputs low coherence light, and in this case the ophthalmologic apparatus does not include an optical member that splits the interference light into spectral components. Regarding the configuration of the interference optical system 30, any known technology may be applied according to the type of OCT.

The optical system 20 may have a configuration for providing a function associated with the examination. For example, the optical system 20 may include a fixation optical system to project a target (fixation target) for fixating the subject's eye E onto the fundus of the subject's eye E.

(Optical Scanner 40)

The optical scanner 40 changes the traveling direction of the measurement light. Under the control of the processor 10 (controller 11), the optical scanner 40 deflects the measurement light in a direction perpendicular to the traveling direction of the measurement light (in a direction intersecting the traveling direction of the measurement light, in a broad sense) according to a predetermined scan pattern. Thereby, a desired site in the fundus or the anterior segment can be scanned with the measurement light according to the scan pattern. The optical scanner 40 includes, for example, a galvanometer mirror for scanning with the measurement light in the x direction, a galvanometer mirror for scanning with the measurement light in the y direction, and a mechanism for driving the galvanometer mirrors independently. Thereby, it is possible to scan with the measurement light in an arbitrary direction in the xy plane.

(Front Lens 51)

The front lens 51 is an optical member for changing the focal point distance of the objective lens 50. The front lens 51 is configured to be capable of inserting/being removed from an optical path toward the subject's eye E. The front lens 51 is removed from the optical path when OCT measurement of the fundus is performed, and is arranged in the optical path when the OCT measurement of the anterior segment is performed. In the embodiments, the front lens 51 is inserted and removed from between the subject's eye E and the objective lens 50, but the front lens 51 may be arranged in between the objective lens 50 and the optical scanner 40. In the case that the front lens 51 is removed from between the subject's eye E and the objective lens 50, the conjugate position of the optical scanner 41 is arranged in the vicinity of the pupil of the subject's eye E, thereby the ophthalmologic apparatus 1 can scan the fundus. In the case that the front lens 51 is arranged between the subject's eye E and the objective lens 50, the conjugate position of the optical scanner 41 is arranged at a position different from the anterior segment Ea of the subject's eye E, thereby the ophthalmologic apparatus 1 can scan the anterior segment Ea.

(Anterior Segment Cameras 60)

The anterior segment cameras 60 photograph the anterior segment Ea of the subject's eye E. As described above, two or more of the anterior segment cameras 60 are provided at positions at which the subject's eye is viewed from different angles with respect to the optical axis of the objective lens 50. Each of the anterior segment cameras 60 is, for example, a video camera for capturing a moving image at a predetermined frame rate. Two or more of the anterior segment cameras 60 photograph the anterior segment Ea from different directions substantially at the same time. In the embodiments, as illustrated in FIG. 3A, FIG. 3B, FIG. 4A, and FIG. 4B, two anterior segment cameras 60A and 60B are provided.

Figure 4A:
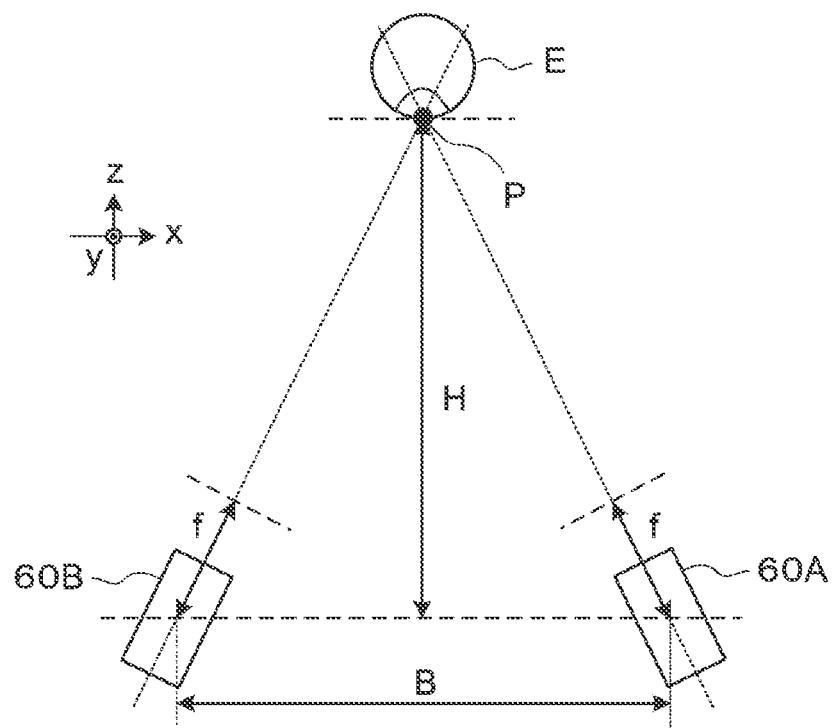
FIG. 4A is a schematic diagram for explaining processing performed by the ophthalmologic apparatus according to the embodiments.
Figure 4B:
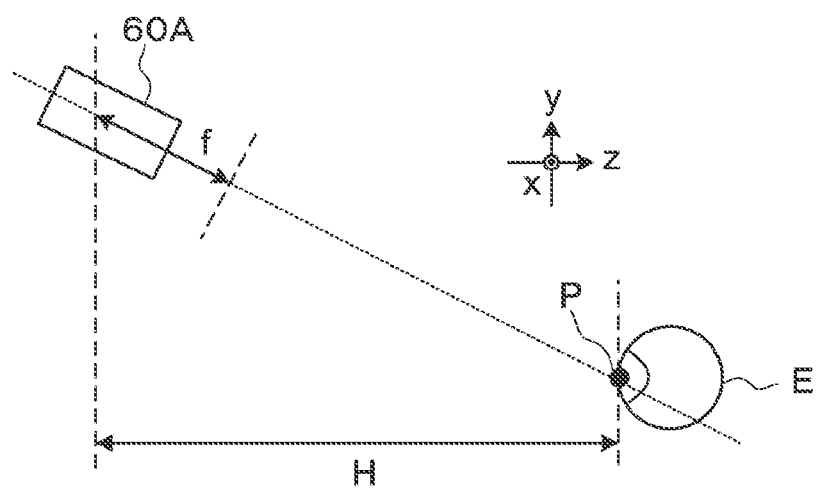
FIG. 4B is a schematic diagram for explaining processing performed by the ophthalmologic apparatus according to the embodiments.

FIG. 4A is a top view illustrating the positional relationship between the subject's eye E and the anterior segment cameras 60A and 60B. Incidentally, +y direction indicates vertically upward, and +z direction indicates the direction of the optical axis of the objective lens 50, that is, a direction toward the subject's eye E from the objective lens 50. FIG. 4B is a side view illustrating the positional relationship between the subject's eye E and the anterior segment cameras 60A and 60B. The anterior segment cameras 60A and 60B are each located at a position off the optical path of the interference optical system 30. In the following, the two anterior segment cameras 60A and 60B may sometimes be collectively represented by reference numeral 60.

There may be any number, at least two, of anterior segment cameras as long as the anterior segment can be substantially simultaneously photographed from two different directions. One anterior segment camera may be arranged coaxially with the objective lens 50.

The phrase "substantially simultaneously" indicates that the deviation in photography timings at a level where the eye movement is negligible is allowed in the photography with two or more anterior segment cameras. Therefore, it is possible for the two or more anterior segment cameras to capture images of the subject's eye E being located in the same position (being faced in the same direction).

While the two or more anterior segment cameras may capture still images as well as moving images, in the embodiments moving image photography is described particularly in detail. In the case of moving image photography, substantially simultaneous photography of the anterior segment as described above can be realized by performing control for synchronizing photography start timings, controlling the frame rates or the capture timings of respective frames, or the like. Meanwhile, in the case of still image photographing, this may be realized by controlling so as to match the timings for photographing.

In the embodiments, two or more photography images substantially simultaneously captured by two or more of the anterior segment cameras 60 are used for performing position matching (alignment) between the optical system 20 and the subject's eye E. The alignment includes Z alignment in the optical axis direction (z direction) of the objective lens 50 and XY alignment in the x direction (horizontal direction) and the y direction (vertical direction) perpendicular to the z direction.

In the embodiments, for each of two or more photography images acquired by the anterior segment cameras 60, a characteristic position corresponding to a characteristic site of the subject's eye E is specified and a three-dimensional position of the characteristic site of the subject's eye E is obtained based on the positions of the anterior segment cameras 60 and the specified characteristic positions in the two or more photography images. Examples of the characteristic sites include a pupil center position, a pupil barycentric position, a corneal center position, a corneal apex position, and the like. In the case of manual alignment, the user operates the user interface unit 90 to relatively move the optical system 20 and the subject's eye E so as to cancel the displacement of the position corresponding to the characteristic site of the subject's eye E with respect to a predetermined alignment (registration) reference position. In the case of auto alignment, the controller 11 controls at least one of the first drive mechanism 80A and the second drive mechanism 80B to relatively move the optical system 20 and the subject's eye E three-dimensionally so as to cancel the displacement of the position corresponding to the characteristic site of the subject's eye E with respect to the alignment (registration) reference position. The alignment reference position may be a position where the optical axis of the optical system 20 approximately coincides with an axis of the subject's eye E and the distance of the optical system 20 with respect to the subject's eye E becomes a predetermined working distance. The working distance is a preset value called working distance of the objective lens 50, and it means the distance between the subject's eye E and the optical system 20 at the time of performing examination using the interference optical system 30.

(Face Support Unit 70)

Figure 3A:
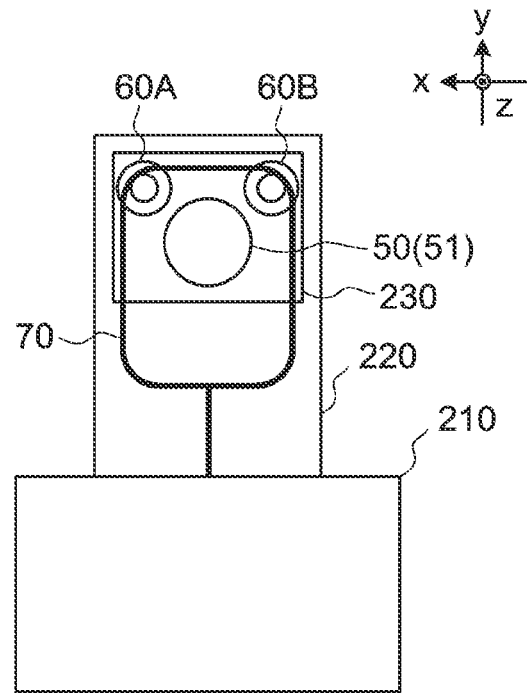
FIG. 3A is a schematic diagram showing an example of the configuration of the ophthalmologic apparatus according to the embodiments.
Figure 3B:
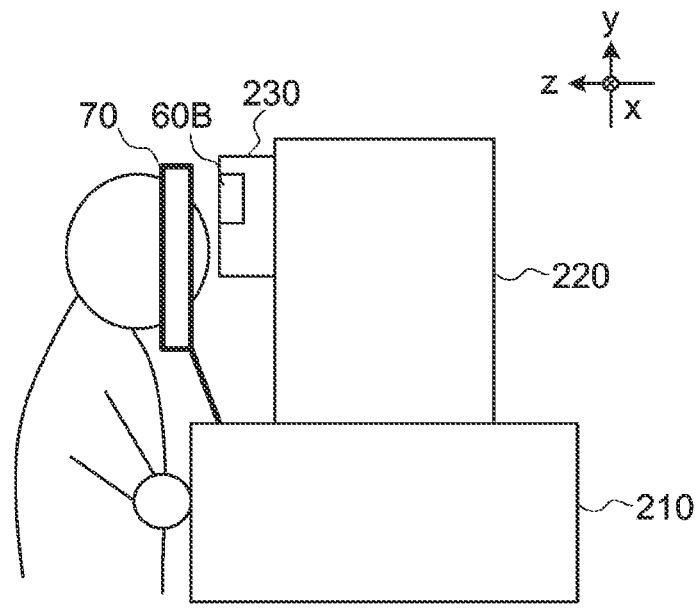
FIG. 3B is a schematic diagram showing an example of the configuration of the ophthalmologic apparatus according to the embodiments.

The face support unit 70 includes a member for supporting the face of the subject. For example, the face support unit 70 includes a forehead rest on which the forehead of the subject is abutted, and a chin rest on which the chin of the subject is placed as shown in FIG. 3A and FIG. 3B. Incidentally, the face support unit 70 may be provided with only one of the forehead rest and the chin rest, or it may include other members than them.

In FIG. 3A and FIG. 3B, drive systems such as the first drive mechanism 80A and the second drive mechanism 80B, and processor 10 are stored in a base 210. The optical system 20 is stored in a casing 220 provided on the base 210. The objective lens 50 is housed in the lens housing unit 230. The lens housing unit 230 is provided so as to be projected on the front surface of the casing 220.

(First Drive Mechanism 80A, Second Drive Mechanism 80B)

The first drive mechanism 80A moves the optical system 20 under the control of the controller 11. The first drive mechanism 80A can move the optical system 20 three-dimensionally. For example, as in the conventional manner, the first drive mechanism 80A includes a mechanism for moving the optical system 20 in the x direction, a mechanism for moving it in the y direction, and a mechanism for moving it in the z direction. The first drive mechanism 80A includes a plurality of stepping motors or the like (driving means) for driving mechanisms for moving in the x direction, the y direction, and the z direction. For example, the controller 11 can supply a driving signal with a predetermined number of pulses to the stepping motors, thereby the optical system 20 moves by a movement amount corresponding to the number of pulses.

The second drive mechanism 80B moves the face support unit 70 under the control of the controller 11. The second drive mechanism 80B can move the face support unit 70 three-dimensionally. The second drive mechanism 80B includes, for example, a mechanism similar to the first drive mechanism 80A. As described above, in general, at least one of the first drive mechanism 80A and the second drive mechanism 80B is provided. Besides, the first drive mechanism 80A may move the optical system 20 three-dimensionally and the second drive mechanism 80B may move the face support unit 70 only in the vertical direction.

(User Interface Unit 90)

The user interface unit 90 provides functions to exchange information between the ophthalmologic apparatus 1 and the user, such as display of information, input of information, input of an operation instruction, and the like. The user interface unit 90 provides output function and input function. Examples of configurations that provide the output function include a display device such as a flat panel display, an audio output device, a print output device, a data writer for writing data to a recording medium, and the like.

Examples of configurations that provide the input function include an operation lever, a button, a key, a pointing device, a microphone, a data reader, and the like. The user interface unit 90 may include a device having the output function and the input function integrated together, such as a touch panel display. The user interface unit 90 may include a graphical user interface (GUI) to input and output information.

(Data Processor 14)

The data processor 14 performs various kinds of data processing and various kinds of analysis processing on an acquired detection result of the interference light or an acquired image. For example, the data processor 14 performs various correction processes such as brightness correction and dispersion correction of images. As described above, the data processor 14 is provided with the analyzer 141.

<Analyzer 141>

The analyzer 141 can perform analysis processing for performing alignment. As an example of a configuration for performing this process, the analyzer 141 is provided with a characteristic position specifying unit 1411.

The analyzer 141 analyzes two or more photography images substantially simultaneously obtained by two or more of the anterior segment cameras 60, thereby the characteristic positions corresponding to the characteristic site of the subject's eye E are obtained. In the embodiments, a moving target position of the optical system 20 is determined based on the obtained characteristic positions and the first drive mechanism 80A and the like are controlled based on the determined moving target position.

<<Characteristic Position Specifying Unit 1411>>

The characteristic position specifying unit 1411 analyzes each photography image, thereby specifying the position (referred to as the characteristic position) in the photography image corresponding to the predetermined characteristic site of the anterior segment Ea. As the predetermined characteristic site, for example, a pupil center position, a pupil barycentric position, a corneal center position, a corneal apex position, or a center position of the subject's eye E may be used. In the following, a specific example of a process for specifying the pupil center position is explained.

First, the characteristic position specifying unit 1411 specifies the image region (pupillary region) corresponding to the pupil of the subject's eye E based on the distribution of the pixel values (luminous values, etc.) in the photography image. Generally, the pupil is represented with lower luminance compared to other sites, so the pupillary region may be specified by searching an image region with low luminance. At this time, the pupillary region may be specified taking into consideration the shape of the pupil. That is, a configuration is possible of specifying the pupillary region by searching a substantially circular image region with low luminance.

Next, the characteristic position specifying unit 1411 specifies the center position of the specified pupillary region. As mentioned above, the pupil is substantially circular; therefore, it is possible to specify the contour of the pupillary region, specify the center position of this contour (an approximate circle or an approximate ellipse thereof), and treat this as the pupil center position. Instead, it is possible to derive the center of gravity of the pupillary region and treat this as the pupil barycentric position.

It should be noted that even when specifying the characteristic position corresponding to other characteristic site, it is possible to specify the characteristic position based on the pixel value distribution of the photography image in the same manner as those mentioned above.

The characteristic position specifying unit 1411 can successively specify the characteristic positions for the photography images successively acquired by the two or more of the anterior segment cameras 60. Further, the characteristic position specifying unit 1411 may specify the characteristic position every one or more arbitrary number of frames for the photography images successively acquired by two or more of the anterior segment cameras 60.

Further, the characteristic position specifying unit 1411 can specify the three-dimensional position of the characteristic site based on the positions of two or more of the anterior segment cameras 60 and the two or more positions corresponding to the characteristic site in the two or more photography images specified by the characteristic position specifying unit 1411. This process is explained with reference to FIG. 4A and FIG. 4B.

In FIG. 4A and FIG. 4B, the distance (baseline length) between the two anterior segment cameras 60A and 60B is represented as "B", and the distance (photographing distance) between the base line of the two anterior segment cameras 60A and 60B and a characteristic site P of the subject's eye E is represented as "H". Further, the distance (screen distance) between each of the anterior segment cameras 60A and 60B and the screen plane is represented as "f".

In this arrangement, the resolution of photography images captured by the anterior segment cameras 60A and 60B is expressed by the following equations. Here, Δp represents the pixel resolution.

$xy$ resolution(planar resolution): $\Delta xy = H \times \Delta p / f$ $z$ resolution(depth resolution): $\Delta z = H \times H \times \Delta p / (B \times f)$ The characteristic position specifying unit 1411 can apply known trigonometry, taking into consideration the positional relationship indicated in FIG. 4A and FIG. 4B, to the positions of the two anterior segment cameras 60A and 60B (these are known) and the characteristic positions corresponding to the characteristic site P in the two photography images, thereby calculating the three-dimensional position of the characteristic site P as the characteristic position.

It should be noted that the photography image to be analyzed by the characteristic position specifying unit 1411 may be an image in which the distortion aberration has been corrected in advance. In this case, the storage unit 12 stores in advance information on distortion aberration occurring in the photography image due to the influence of the optical system mounted on the anterior segment cameras 60, for each of the anterior segment cameras 60. The photography image is corrected based on the information stored in the storage unit 12.

The characteristic position specified by the characteristic position specifying unit 1411 is sent to the controller 11 as the moving target position. The controller 11 controls at least one of the first drive mechanism 80A and the second drive mechanism 80B based on the moving target position, so that the position in the x direction and the y direction of the optical axis of the optical system 20 coincides with the moving target position in the x direction and the y direction, and the distance in the z direction becomes a predetermined working distance.

Further, the analyzer 141 can perform analysis processing for perform OCT measurement of the fundus and the anterior segment. The ophthalmologic apparatus 1 according to the embodiments perform radial scan with respect to the anterior segment Ea to perform OCT measurement of the anterior segment Ea (that is, the front lens 51 is arranged between the subject's E and the objective lens 50). Hereinafter, the OCT measurement with respect to the anterior segment Ea will be mainly described, however the OCT measurement with respect to the fundus of the subject's eye E in a state in which the front lens 51 is removed from between the subject's eye E and the objective lens 50 is performed in the same manner.

Figure 5:
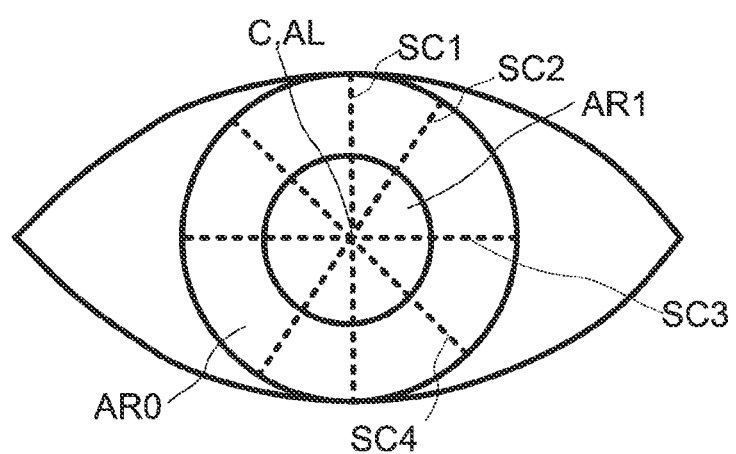
FIG. 5 is a schematic diagram for explaining the operation of the ophthalmologic apparatus of the embodiments.

FIG. 5 is an explanatory diagram of the radial scan according to the embodiments. FIG. 5 schematically shows the trajectory of the projection position of the measurement light in the radial scan performed on the anterior segment Ea of the subject's eye E. In FIG. 5, the iris region AR0 and the pupillary region AR1 are represented. In the radial scan, a plurality of scans are performed radially around a predetermined scan center position C. FIG. 5 shows a case where four scans are radially performed around the scan center position C, however, in general, more than 16 scans are performed. The scan SC1 represents a scan in the vertical direction. The scan SC2 represents a scan in a direction rotated clockwise by 45° with respect to the vertical direction around the scan center position C. The scan SC3 represents a scan in a direction rotated clockwise by 90° with respect to the vertical direction around the scan center position C. The scan SC4 represents a scan in a direction rotated clockwise by 135° with respect to the vertical direction around the scan center position C.

The scan center position C is usually arranged on the optical axis of the objective lens 50. When the optical axis of the objective lens 50 substantially coincides with the alignment reference position (registration reference position) AL, the alignment is completed and the scan center position C substantially coincides with the alignment reference position AL. The alignment reference position may be the pupil center position, the pupil barycentric position, the corneal center position, the corneal apex position, or the center position of the subject's eye. FIG. 5 shows a state in which the alignment is completed and the scan center position C substantially coincides with the alignment reference position AL (in this case, the center position (pupil center position) of the pupillary region AR1) in the subject's eye E. The analyzer 141 can obtain corneal surface shape, corneal inner surface shape, corneal thickness, anterior chamber depth, and the like from the cross-sectional shape of each meridian represented in the tomographic image acquired by each scan as shown in FIG. 5, and calculate two-dimensional distribution of them or three-dimensional distribution of them.

For example, the OCT measurement on the anterior segment Ea of the subject's eye E is started when the alignment of the optical system 20 with respect to the subject's eye E is completed. In the ophthalmologic apparatus 1, it is determined that the alignment is completed when the relative position between the subject's eye E and the optical system 20 is within a predetermined range based on the two or more characteristic positions in the two or more photography images acquired by two or more of the anterior segment cameras 60. Thereby, the scan center position C coincides with the alignment reference position AL. When it is determined that the alignment is completed, the radial scan shown in FIG. 5 is started. Since the optical system 20 does not move during scanning, the scan center position C of the scan pattern is fixed. Without the movement of the subject's eye E, the radial scan is performed radially around the alignment reference position AL of the subject's eye E.

However, the subject's eye may move due to the involuntary eye movement or the like during the OCT measurement (performing the radial scan).

Figure 6:
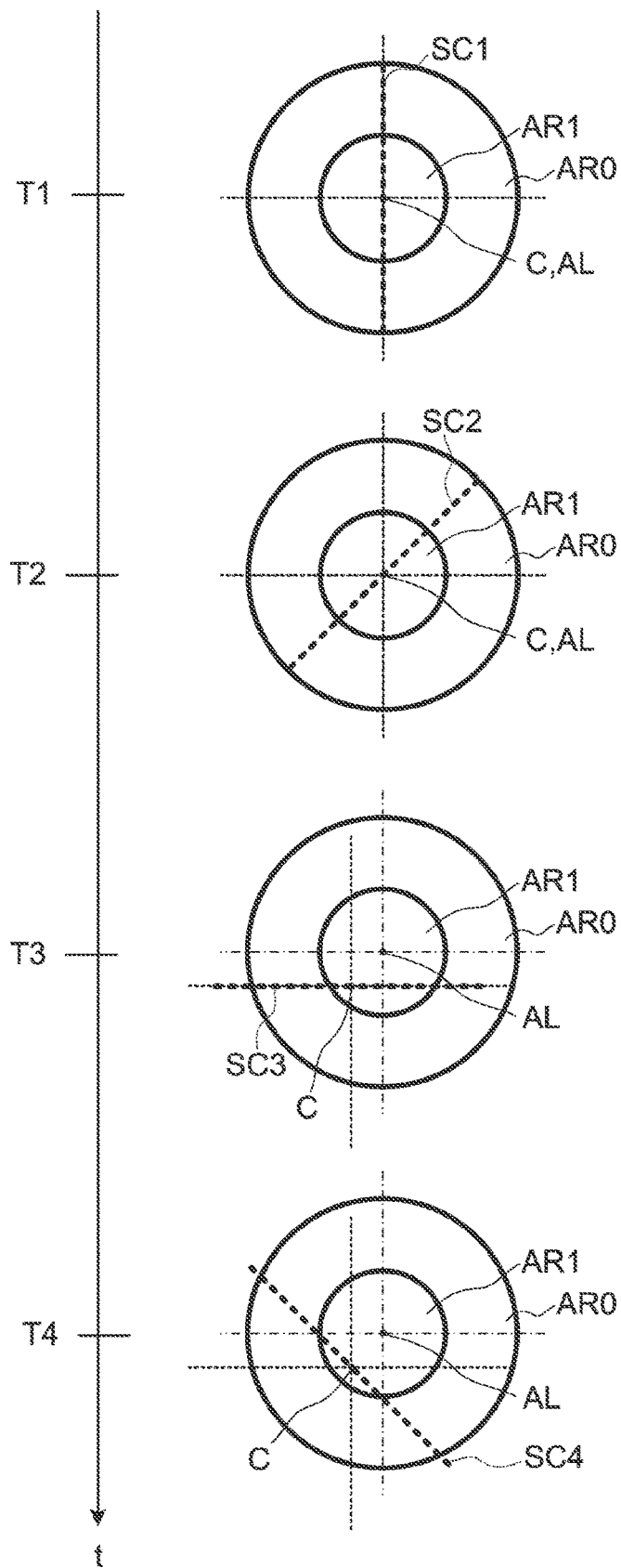
FIG. 6 is a schematic diagram for explaining radial scan.

FIG. 6 schematically shows scan positions of the radial scan when the subject's eye E moves during the OCT measurement. FIG. 6 schematically represents the scan positions when the scans SC1 to SC4 shown in FIG. 5 are performed at the times T1 to T4. In FIG. 6, for example, it is assumed that the subject's eye E has moved obliquely upward between the times T2 and T3.

At the times T1 and T2, the scans SC1 and SC2 are performed in a state in which the scan center position C substantially coincides with the alignment reference position AL (that is, the characteristic position of the subject's eye E). In the scans SC1 and SC2, data corresponding to scan lines passing through the alignment reference position AL (in this case, the pupil center position) are acquired.

On the other hand, at the time T3, the scan SC3 is performed below the alignment reference position AL. Similarly, at the time T4, the scan SC4 is performed obliquely downward with respect to the alignment reference position AL. That is, at the times T3 and T4, the scan center position C moves, thereby data corresponding to scan lines that do not pass thorough the alignment reference position AL are acquired in the scans SC3 and SC4.

Figure 7:
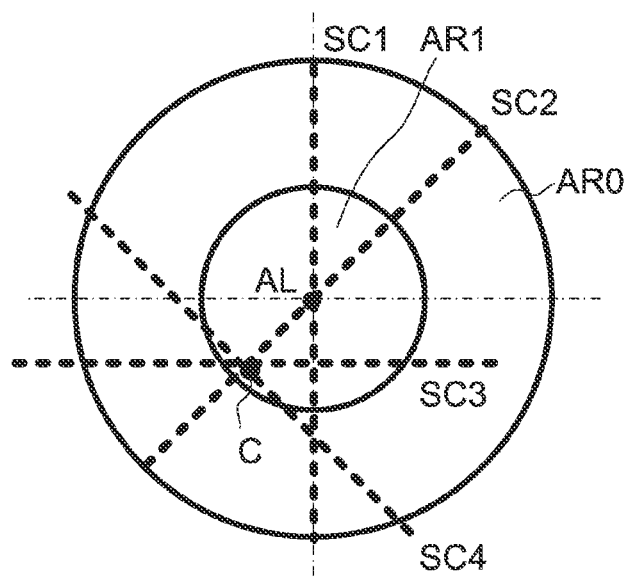
FIG. 7 is a schematic diagram for explaining the operation of the ophthalmologic apparatus of the embodiments.

As a result, despite the fact that the scan is performed radially intersecting at the alignment reference position AL of the subject's eye E as shown in FIG. 5, data of scan lines whose scan positions are shifted with respected to the alignment reference position AL (pupil center position) are acquired actually as shown in FIG. 7. It is impossible to obtain an accurate property distribution, even if the shape, thickness, or the like of the cornea in the anterior segment Ea is obtained on the assumption that the data acquired in this manner is data acquired when all the scans pass through the alignment reference position AL.

Therefore, the analyzer 141 according to the embodiments performs processing for correcting the positional displacement of the scan position from the scan result itself when the subject's eye moves due to the involuntary eye movement, the line-of-sight deviation, or the like during scanning. As an example of a configuration for performing processing for correcting the positional displacement of the scan position, the analyzer 141 is provided with the characteristic region analyzer 1412, the movement amount specifying unit 1413, the movement direction specifying unit 1414, and the positional displacement correcting unit 1415.

<<Characteristic Region Analyzer 1412>>

The characteristic region analyzer 1412 specifies the characteristic region from the anterior segment image(s) acquired by the anterior segment cameras 60 and obtains a predetermined reference value by analyzing the specified characteristic region. At this time, since the anterior segment cameras 60 observe from the different angles with respect to the optical axis of the optical system 20, it is desirable to obtain the reference value by correcting the distortion of the angle to be viewed with respect to the acquired image(s). Examples of the characteristic region include a region corresponding to the pupil (pupillary region), a region corresponding to the cornea (corneal region), a region corresponding to the iris, and the like. The characteristic region may be the same region as the region including the characteristic site specified by the characteristic position specifying unit 1411. The reference value is a value corresponding to a scan length. The scan length is a length of a scan range in a B scan direction (in a direction perpendicular to the traveling direction of the measurement light) within the characteristic region of the scan which passes through the reference position of the subject's eye E. The reference value may be a value corresponding to a pupil diameter, an iris outer diameter, or a distance between corner angles obtained by performing scan which passes through the reference position. In the following embodiments, a description is given of a case of employing the pupil diameter as the reference value. The reference position may be the same as the above characteristic position (that is, the pupil center position). The reference position may be the pupil center position, the pupil barycentric position, the corneal center position, the corneal apex position, or the center position of the subject's eye.

The characteristic region analyzer 1412 can obtain the scan length for each of the plurality of scans performed in the radial scan.

It should be noted that the reference value may not be a value obtained by the characteristic region analyzer 1412 but may be a value acquired in advance or an average value.

<<Movement Amount Specifying Unit 1413>>

The movement amount specifying unit 1413 obtains the scan length within the above characteristic region by analyzing the detection result of the interference light corresponding to at least one of the plurality of scans performed in the radial scan, the detection result being acquired by the interference optical system 30. The movement amount specifying unit 1413 can obtain the above scan length by analyzing the tomographic image formed by the image forming unit 13 based on the detection result of the interference light corresponding to the scan(s). The movement amount specifying unit 1413 specifies, as the movement amount of the subject's eye E, a movement amount of the scan with respect to the reference position by comparing the obtained scan length with the reference value (scan length) of the scan obtained by the characteristic region analyzer 1412.

Figure 8A:
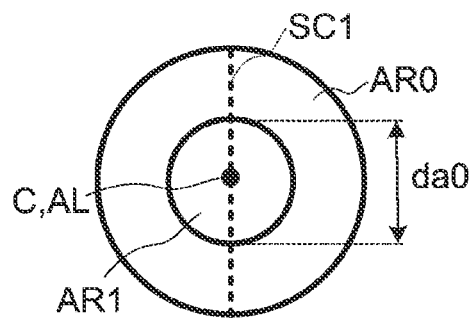
FIG. 8A is a schematic diagram for explaining the operation of the ophthalmologic apparatus of the embodiments.
Figure 8A:
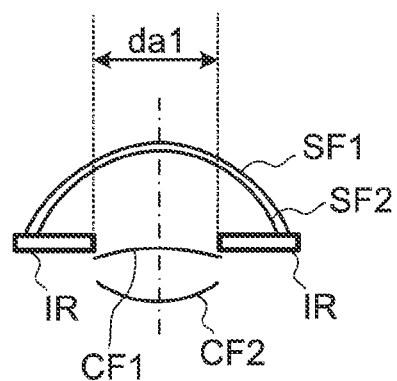
Figure 8B:
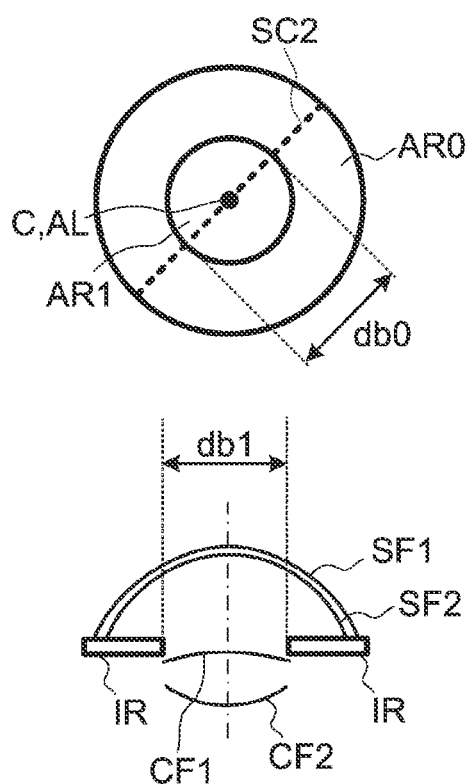
FIG. 8B is a schematic diagram for explaining the operation of the ophthalmologic apparatus of the embodiments.
Figure 8C:
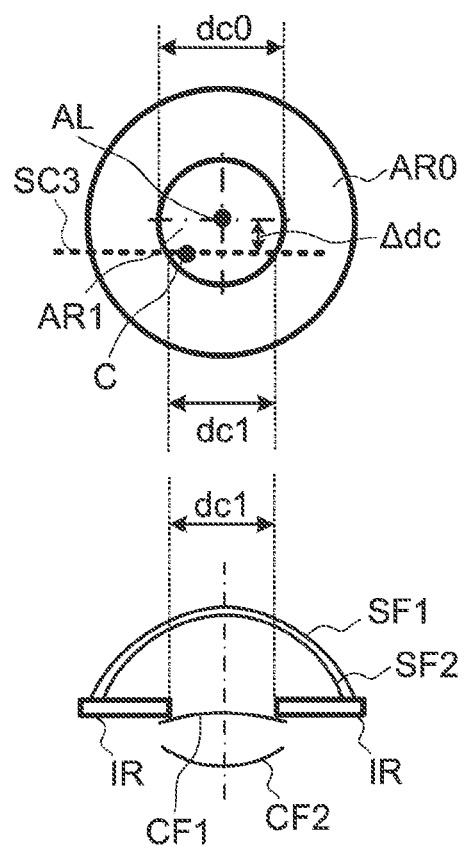
FIG. 8C is a schematic diagram for explaining the operation of the ophthalmologic apparatus of the embodiments.
Figure 8D:
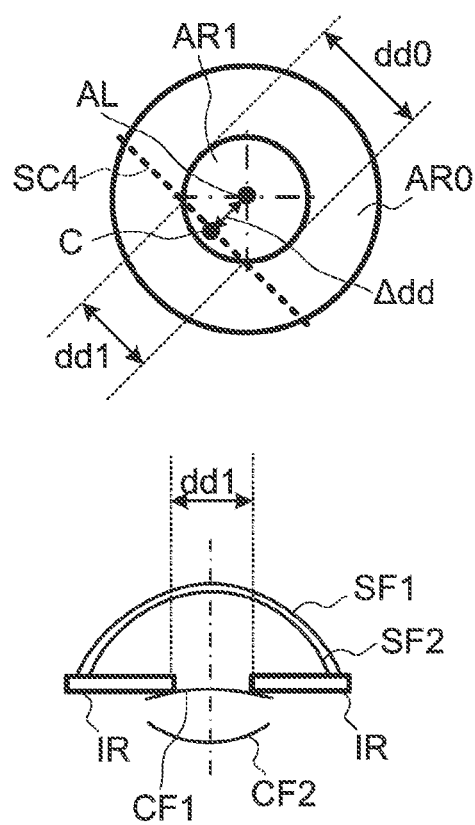
FIG. 8D is a schematic diagram for explaining the operation of the ophthalmologic apparatus of the embodiments.

FIG. 8A, FIG. 8B, FIG. 8C, and FIG. 8D schematically show a relationship between the reference value and the scan length in each scan of FIG. 5. FIG. 8A schematically represents the reference value and the scan length corresponding to the scan SC1. FIG. 8B schematically represents the reference value and the scan length corresponding to the scan SC2. FIG. 8C schematically represents the reference value and the scan length corresponding to the scan SC3. FIG. 8D schematically represents the reference value and the scan length corresponding to the scan SC4. In each of FIG. 8A, FIG. 8B, FIG. 8C, and FIG. 8D, an anterior segment image is illustrated upward and a tomographic image representing a cross section of the scan is illustrated downward. In the tomographic images of FIG. 8A, FIG. 8B, FIG. 8C, and FIG. 8D, the corneal surface SF1, the corneal back surface SF2, the crystalline lens front surface CF1, the crystalline lens posterior surface CF2, and the iris IR are represented.

The movement amount specifying unit 1413 analyzes the tomographic image formed based on the detection result of the interference light acquired by the scan SC as shown in FIG. 8A and obtains the distance (pupil cutting length) da1 between the irises which is a distance between the edges of the iris IR. Since the scan SC1 is a scan passing through the pupil center position, the reference value da0, which is obtained by the characteristic region analyzer 1412, corresponds to the pupil diameter and this substantially coincides with the distance da1 between the irises. Therefore, the movement amount specifying unit 1413 specifies the movement amount of the subject's eye E in the direction perpendicular to the scan direction (B scan direction) of the scan SC1 as zero.

In the same manner, the movement amount specifying unit 1413 analyzes the tomographic image formed based on the detection result of the interference light acquired by the scan SC2 as shown in FIG. 8B and obtains the distance db between the irises which is a distance between the edges of the iris IR. Since the scan SC2 is a scan passing through the pupil center position, the reference value db0, which is obtained by the characteristic region analyzer 1412, corresponds to the pupil diameter and this substantially coincides with the distance db1 between the irises. Therefore, the movement amount specifying unit 1413 specifies the movement amount of the subject's eye E in the direction perpendicular to the scan direction of the scan SC2 as zero.

Furthermore, the movement amount specifying unit 1413 analyzes the tomographic image formed based on the detection result of the interference light acquired by the scan SC3 as shown in FIG. 8C and obtains the distance dc1 between the irises which is a distance between the edges of the iris IR. Since the scan SC3 is a scan that does not pass through the pupil center position, the reference value dc (that is, the pupil diameter), which is obtained by the characteristic region analyzer 1412, becomes larger than the distance dc1 between the irises. The ratio of the distance dc1 between the irises to the reference value dc0 corresponds to the distance in the direction perpendicular to the scan direction of the scan SC3. Therefore, the movement amount specifying unit 1413 can specify the movement amount $\Delta dc$ of the subject's eye E in the direction perpendicular to the scan direction of the scan SC3 from the ratio of the distance dc1 between the irises to the reference value dc0.

In the same manner, the movement amount specifying unit 1413 analyzes the tomographic image formed based on the detection result of the interference light acquired by the scan SC4 as shown in FIG. 8D and obtains the distance dd1 between the irises which is a distance between the edges of the iris IR. Since the scan SC4 is a scan that does not pass through the pupil center position, the reference value dd0 (that is, the pupil diameter), which is obtained by the characteristic region analyzer 1412, becomes larger than the distance dd1 between the irises. The ratio of the distance dd1 between the irises to the reference value dd0 corresponds to the distance in the direction perpendicular to the scan direction of the scan SC4. Therefore, the movement amount specifying unit 1413 can specify the movement amount $\Delta dd$ of the subject's eye E in the direction perpendicular to the scan direction of the scan SC4 from the ratio of the distance dd1 between the irises to the reference value dd0.

The movement amount specifying unit 1413 can specify the two-dimensional movement amount of the subject's eye E by specifying the movement amount for two or more scans with different scan directions each other.

<<Movement Direction Specifying Unit 1414>>

The movement direction specifying unit 1414 specifies the movement direction of the subject's eye E for at least one of the plurality of scans performed in the radial scan, based on the position of the scan range within the pupillary region in the entire scan range in the B scan direction of the at least one scan.

Figure 9A:
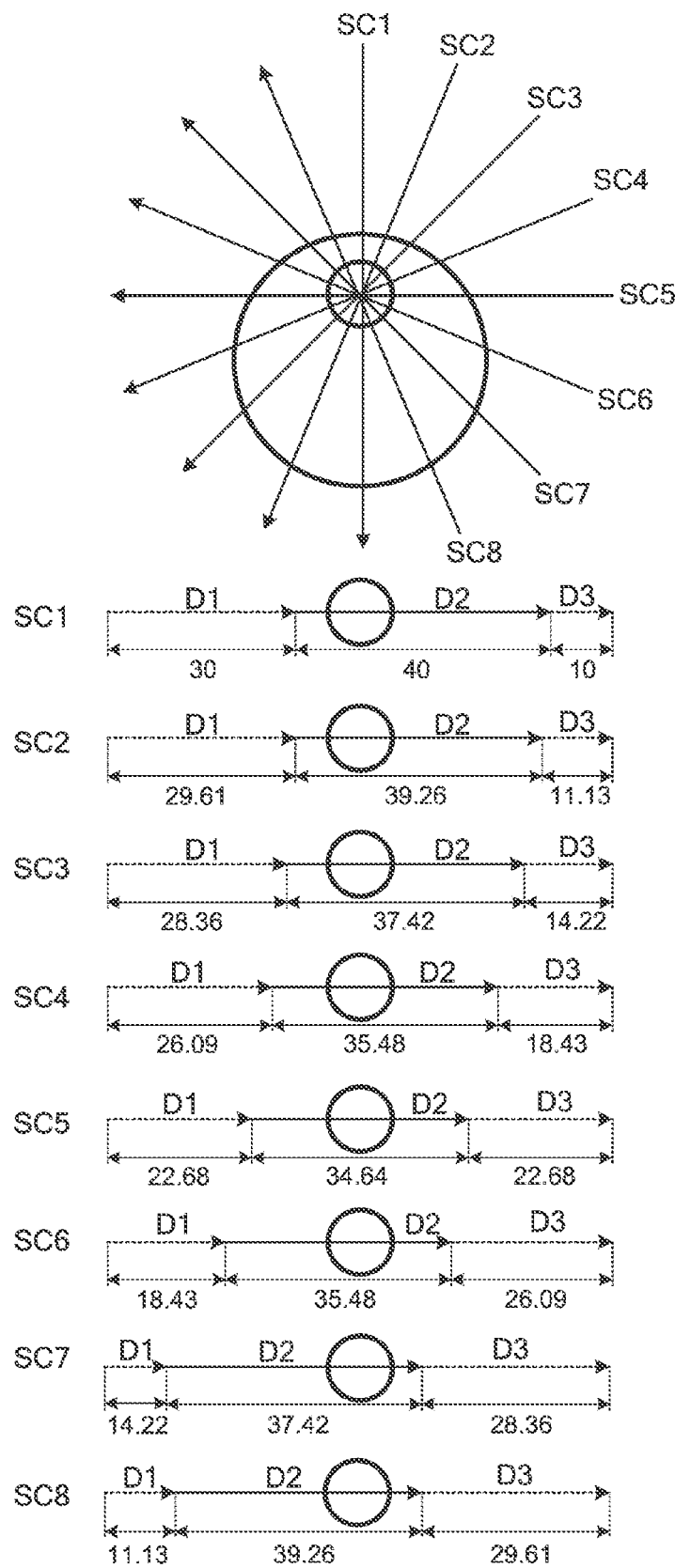
FIG. 9A is a schematic diagram for explaining the operation of the ophthalmologic apparatus of the embodiments.
Figure 9B:
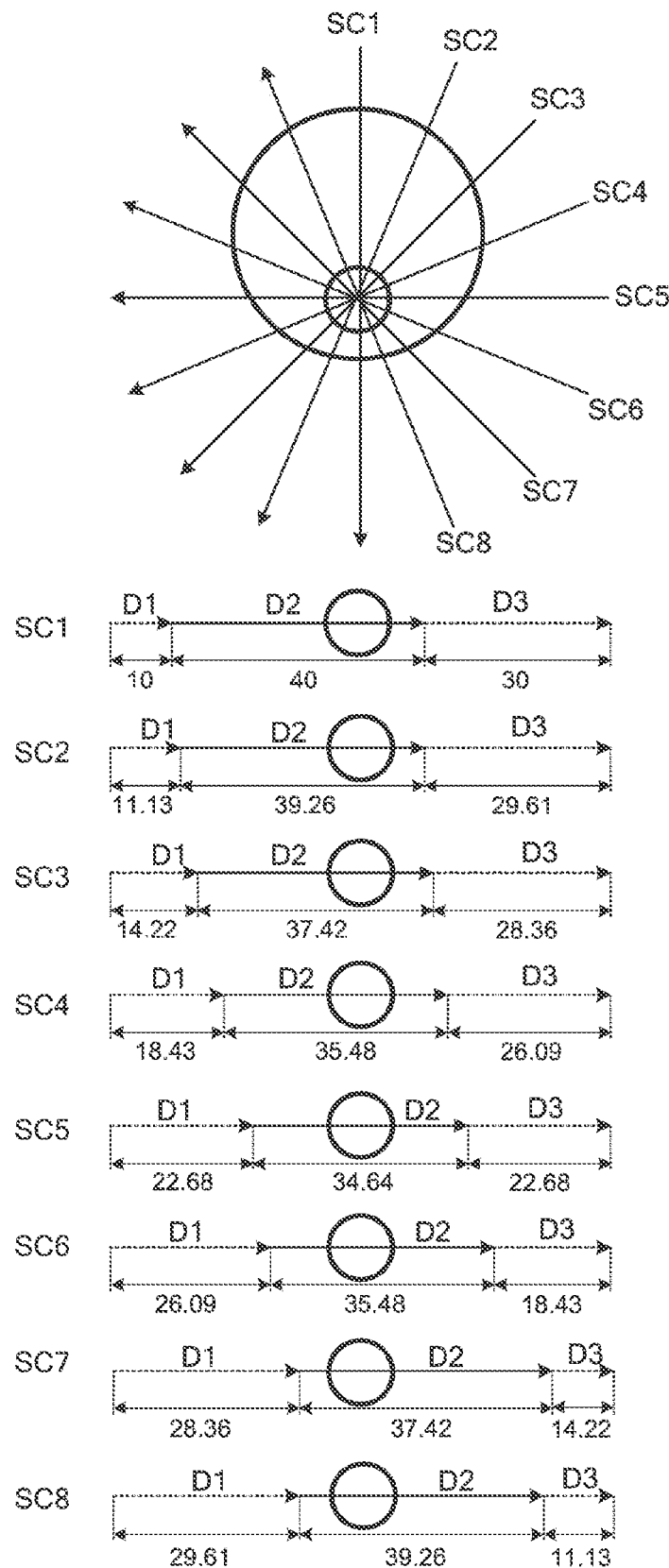
FIG. 9B is a schematic diagram for explaining the operation of the ophthalmologic apparatus of the embodiments.

FIG. 9A and FIG. 9B show operation diagrams of the movement amount specifying unit 1413. FIG. 9A schematically shows the positions of the entire scan range and the scan range within the pupillary region for each scan of the radial scan when the pupil center position moves upward in the vertical direction with respect to the scan center position C. FIG. 9B schematically shows the positions of the entire scan range and the scan range within the pupillary region for each scan of the radial scan when the pupil center position moves downward in the vertical direction with respect to the scan center position C. In FIG. 9A and FIG. 9B, it is assumed that eight scans SC1 to SC8 are performed in the radial scan, for convenience of explanation.

In FIG. 9A and FIG. 9B, for each scan, the scan length from the scan start position to the boundary position of the pupillary region is denoted as D1, the scan length within the pupillary region is denoted ad D2, and the scan length from the boundary position of the pupillary region to the scan end position is denoted as D3. The scan length D2 is specified by the movement amount specifying unit 1413. For convenience of explanation, the total scan length of each scan is 80, and each scan length is represented by a numerical value.

As shown in FIG. 9A and FIG. 9B, the position of the scan range within the pupillary region in the entire scan range of each scan changes according to the angle with respect to a predetermined direction (for example, the vertical direction). In FIG. 9A, the position of the scan range within the pupillary region in the entire scan range shifts toward the scan start position, as the angle with respect to the vertical direction increases from the scan SC1 to the scan SC8. On the other hand, in FIG. 9B, the position of the scan range within the pupillary region in the entire scan range shifts toward the scan end position, as the angle with respect to the vertical direction increases from the scan SC to the scan SC8.

The position of the scan range within the pupillary region in the entire scan range corresponds to the ratio between the scan length D1 and the scan length D3. In case of FIG. 9A and FIG. 9B, the ratio between the scan length D1 and the scan length D3 is reversed except for the scan SC5 that performs scan in the direction perpendicular to the movement direction of the subject's eye E, when the angle with respect to the vertical direction increases from the scan SC1 to the scan SC8. Therefore, since the angle with respect to the vertical direction is known for each scan, the movement direction can be specified from the ratio between the scan length D1 and the scan length D3. It should be noted that the movement direction perpendicular to the scan direction can be specified from the ratio between the scan length D1 and the scan length D3 in each of two or more scans with different scan directions each other.

<<Positional Displacement Correcting Unit 1415>>

The positional displacement correcting unit 1415 corrects the scan position(s) of the plurality of scans performed in the radial scan so as to cancel the movement amount specified by the movement amount specifying unit 1413 in the movement direction specified by the movement direction specifying unit 1414.

The analyzer 141 includes the property distribution calculator 1416 that calculates the property information of the subject's eye E from the result of scan in which the positional displacement correcting process of the scan position has been performed as describe above.

<<Property Distribution Calculator 1416>>

The property distribution calculator 1416 obtains the distribution of the property information of the anterior segment Ea by using the detection result of the interference light in which the positional displacement with respect to the pupil center position is corrected, based on the specified movement amount and the specified movement direction as described above. The property information includes at least one of corneal shape information, corneal thickness information, and anterior chamber depth information.

For example, the property distribution calculator 1416 obtains the shape of the corneal surface, the shape of the corneal back surface, and the corneal thickness by a known method using the detection result of the interference light in which the positional displacement of the scan position is corrected. The property distribution calculator 1416 generates information representing a two-dimensional distribution by associating information representing the obtained shape of the corneal surface and the like with the x coordinate position and the y coordinate position. Furthermore, the property distribution calculator 1416 may generate information representing a three-dimensional distribution by associating information representing the obtained shape of the corneal surface and the like with the x coordinate position, the y coordinate position, and the z coordinate position.

Further, the property distribution calculator 1416 may obtain the shape of the corneal surface, the shape of the corneal back surface, and the corneal thickness by a known method using the detection result of the interference light and then may generate information representing the two-dimensional distribution by correcting the positional displacement with respect to the information representing the obtained shape of the corneal surface and the like. In the same manner, the property distribution calculator 1416 may generate information representing the three-dimensional distribution by correcting the positional displacement with respect to the information representing the obtained shape of the corneal surface and the like.

The data processor 14 that functions as above includes, for example, a processor, a RAM, a ROM, a hard disk drive, a circuit board, and the like. In a storage device such as the hard disk drive, a computer program for causing the processor to execute the functions described above is stored in advance.

The region (pupillary region) corresponding to the pupil of the subject's eye E is an example of the "characteristic region" according to the embodiments. The direction perpendicular to the traveling direction of the measurement light, or the B scan direction is an example of the "intersecting direction" according to the embodiments. The value corresponding to the scan length which is a length of the scan range in the B scan direction within the pupillary region of the scan which passes through the pupil center position is an example of the "reference value" according to the embodiments. The pupil center position of the subject's eye E is an example or the "reference position" according to the embodiments. At least one of the first drive mechanism 80A and the second drive mechanism 80B is an example of the "movement mechanism" according to the embodiments. The anterior segment cameras 60 are examples of the "anterior segment imaging system" according to the embodiments. The characteristic analyzer 1412 is an example of the "first specifying unit" according to the embodiments. At least one of the movement amount specifying unit 1413 and the movement direction specifying unit 1414 is an example of the "second specifying unit" according to the embodiments.

[Operation]

The operation of the ophthalmic apparatus 1 will be described.

Figure 10:
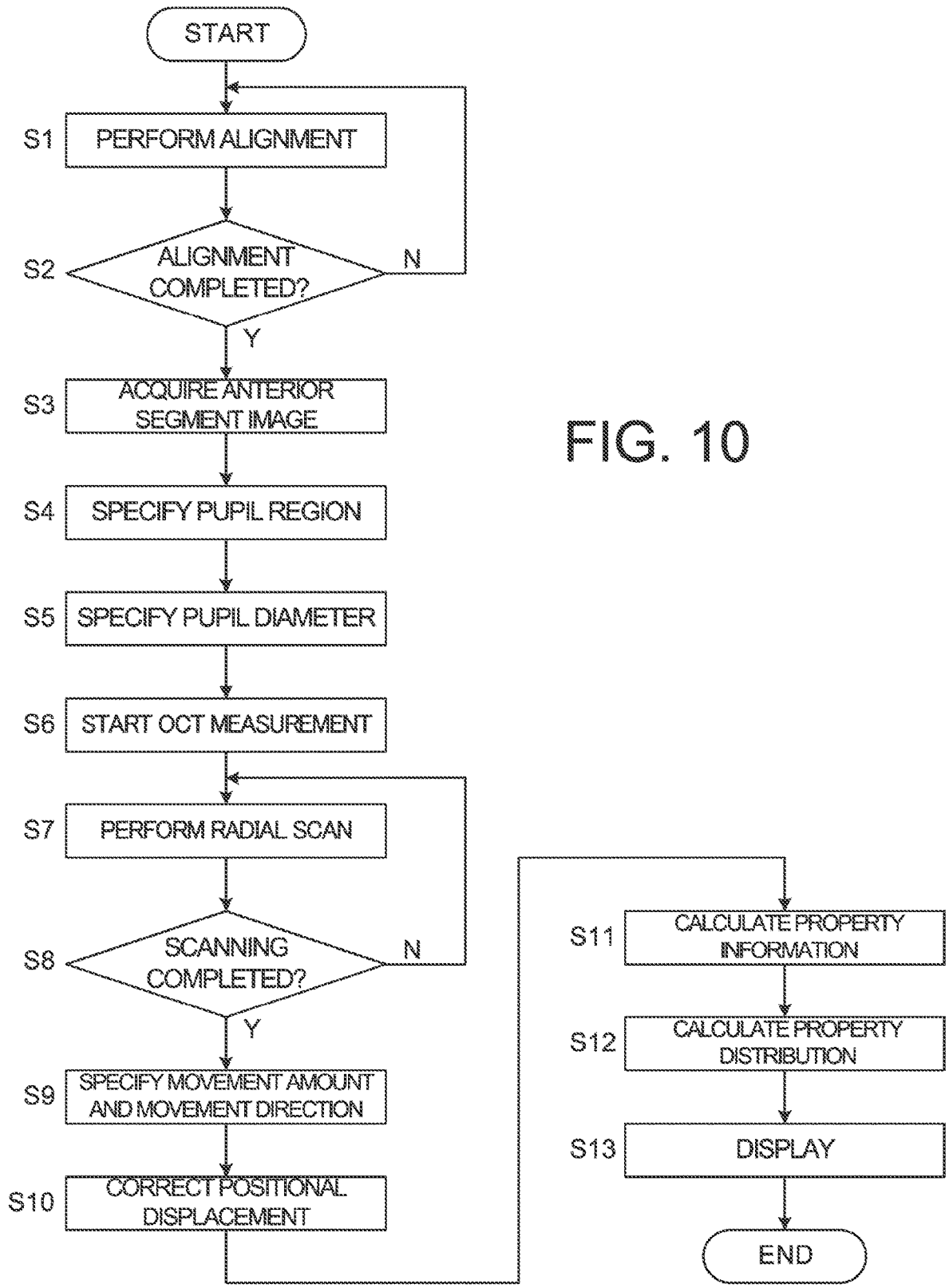
FIG. 10 is a flowchart showing an operational example of the ophthalmologic apparatus according to the embodiments.

FIG. 10 illustrates an example of the operation of the ophthalmologic apparatus 1.

(Step S1)

When the user operates the user interface unit 90 for instructing to start the OCT measurement, the ophthalmologic apparatus 1 starts performing alignment. The alignment start instruction may be automatically performed by the controller 11.

Once the instruction for commencing automatic alignment is given, the controller 11 causes the respective anterior segment cameras 60A and 60B to commence photographing of the anterior segment Ea. This photographing is moving image photography of the anterior segment Ea as the photography subject. Each of the anterior segment cameras 60A and 60B performs moving image photography at a predetermined frame rate. Here, the timings of photographing by the anterior segment cameras 60A and 60B may be synchronized by the controller 11. The respective anterior segment cameras 60A and 60B successively transmit the acquired frames to the controller 11 in real time. The controller 11 associates the frames obtained by both anterior segment cameras 60A and 60B in accordance with the photography timing. That is, the controller 11 associates the frames substantially and simultaneously acquired by both anterior segment cameras 60A and 60B with each other. This association is carried out based on, for example, the abovementioned synchronous control or based on the input timings of the frames from the anterior segment cameras 60A and 60B. The controller 11 transmits a pair of the associated frames to the analyzer 141. The analyzer 141 analyzes each frame.

In the case of the auto alignment, the characteristic position specifying unit 1411 analyzes each frame and performs processing for specifying the pupillary region corresponding to the pupil of the anterior segment Ea in the anterior segment image acquired in step S1. The characteristic position specifying unit 1411 specifies the pupillary region as described above and specifies the pupil center position within the specified pupillary region as the characteristic position. Sequentially, the controller 11 controls the analyzer 141 to specify the positional displacement amount and the positional displacement direction between the position corresponding to the optical axis of the optical system 20 and the pupil center position. Further, the controller 11 controls at least one of the first drive mechanism 80A and the second drive mechanism 80B so as to cancel the specified positional displacement amount, thereby the optical system 20 and the subject's eye E is moved relatively.

In the case of the manual alignment, the controller 11 controls at least one of the first drive mechanism 80A and the second drive mechanism 80B to relatively move the optical system 20 and the subject's eye E, according to the user's operation content with respect to the user interface unit 90. In this case, the user can perform alignment using the user interface unit 90 while referring to the displayed observation image. The user moves the optical system 20 relative to the subject's eye E by operating the user interface unit 90 so that the image of the pupil appears in the observation image.
(Step S2)

The controller 11 determines whether or not the position matching of the optical system 20 with respect to the subject's eye E is completed. The controller 11 can determine whether or not the position matching of the optical system 20 with respect to the subject's eye E is completed by determining whether or not the positional displacement amount specified in step S1 is equal to or less than a predetermined threshold value.

When it is determined that the position matching of the optical system 20 with respect to the subject's eye E is completed (step S2: Y), the operation of the ophthalmologic apparatus 1 moves step S3. When it is determined that the position matching of the optical system 20 with respect to the subject's eye E is not completed (step S2: N), the operation of the ophthalmologic apparatus 1 moves step S1.

(Step S3)

When it is determined that the position matching of the optical system 20 with respect to the subject's eye E is completed in step S2 (step S2: Y), the controller 11 controls the anterior segment cameras 60 to acquire the anterior segment images of the subject's eye E. It should be noted that the anterior segment image acquired in step S2 may be used as it is, in step S3.
(Step S4)

The controller 11 controls the characteristic analyzer 1412 to specify the pupillary region in the anterior segment images acquired in step S3.
(Step S5)

Sequentially, the characteristic region analyzer 1412 analyzes the pupillary region specified in step S4 to specify the pupil center position, and specifies the pupil diameter for the scan direction passing through the specified the pupil center position. That is, the characteristic region analyzer 1412 specifies the pupil diameter as the value corresponding to the scan length which is a length of the scan range in the B scan direction within the pupillary region of the scan which passes through the pupil center position. Here, since the anterior segment cameras 60 view the anterior segment obliquely from the front, the pupil images represented in the acquired images are deformed. Since the visual angles of the anterior segment cameras 60 are known from a design point of view, the pupil diameter in each meridian direction is corrected to a length viewed from the front, taking into account the visual angle.
(Step S6)

Next, the controller 11 controls the interference optical system 30 to start the OCT measurement.
(Step S7)

The controller 11 controls the optical scanner 40 according to the predetermined scan pattern to start performing radial scan on the anterior segment Ea of the subject's eye E. The controller 11 causes the respective scans shown in FIG. 5 to be performed in sequence.
(Step S8)

The controller 11 determines whether the scanning is completed or not. The controller 11 can determine whether the scanning is completed or not based on the predetermined scan pattern. When it is determined that the scanning is completed (step S8: Y), the operation of the ophthalmologic apparatus 1 moves step S9. When it is determined that the scanning is not completed (step S8: N), the operation of the ophthalmologic apparatus 1 moves step S7.
(Step S9)

When it is determined that the scanning is completed in step S8 (step S8: Y), the controller 11 controls the movement amount specifying unit 1413 to specify the movement amount of the subject's eye E as described above and controls the movement direction specifying unit 1414 to specify the movement direction of the subject's eye E, for each scan performed in step S7. In step S9, the movement amount and the movement direction are specified from the tomographic image formed by the image forming unit 13.
(Step S10)

Sequentially, the controller 11 controls the positional displacement correcting unit 1415 to correct the scan position based on the movement amount and the movement direction specified respectively in step S9, for each scan.
(Step S11)

The controller 11 causes the property information to be calculated based on the detection result of the interference light of each scan in which the positional displacement is corrected in step S10.

(Step S12)

The controller 11 controls the property distribution calculator 1416 to calculate the property distribution information representing the distribution of the property information calculated in step S11.

(Step S13)

The controller 11 controls the display unit of the user interface unit 90 to display the property distribution corresponding to the property distribution information calculated in step S12. This terminates the operation of the ophthalmologic apparatus (END).

As described above, according to the embodiments, even when the subject's eye moves due to the involuntary eye movement, the line-of-sight deviation, or the like during performing radial scan, the positional displacement of the scan position can be corrected from the scan result itself. Thereby, it becomes possible to obtain (acquire) the data of the anterior segment accurately.

It should be noted that the case where the data of the anterior segment Ea of the subject's eye E is acquired has been described, but the embodiments can be applied to the case where the data of the fundus of the subject's eye E is acquired.

[Effects]

The effects of the ophthalmologic apparatus according to the embodiments are explained.

An ophthalmologic apparatus (1) according to the embodiments includes an optical scanner (40), an interference optical system (30), a controller (11), and an analyzer (141). The interference optical system splits light from a light source into measurement light and reference light, projects the measurement light onto a subject's eye (E) via the optical scanner, and detects interference light generated from returning light of the measurement light from the subject's eye and the reference light. The controller controls the optical scanner so as to perform scan by the measurement light in an intersecting direction (B scan direction) which intersects a traveling direction of the measurement light. The analyzer specifies a scan length based on a detection result of the interference light corresponding to the scan, the detection result being acquired by the interference optical system, the scan length being a length of a scan range in the intersecting direction within a characteristic region (pupillary region AR1) in an anterior segment (Ea) of the subject's eye, and specifies a movement amount of the subject's eye based on a reference value of the characteristic region and the scan length. The interference optical system splits light from a light source into measurement light and reference light, and detects interference light generated from returning light of the measurement light from the patient's eye and the reference light.

According to such a configuration, while deflecting the measurement light in the intersecting direction which intersects the traveling direction, the scan length in the intersecting direction within the characteristic region of the anterior segment can be specified. Thereby the movement amount of the subject's eye corresponding to the scan length with reference to the reference value of the characteristic region can be specified. As a result, the movement amount of the subject's eye can be specified from the scan result itself. Therefore, even when the subject's eye moves due to the involuntary eye movement, the line-of-sight deviation, or the like during scanning, it becomes possible to acquire the data of the anterior segment accurately in consideration of the movement amount of the subject's eye, without the error effect due to the deviation between the acquiring timing of the images and the scan timing.

Further, in the ophthalmologic apparatus according to the embodiments, the analyzer may specify a movement direction of the subject's eye based on a position of the scan range within the characteristic region in an entire scan range of the scan.

According to such a configuration, the movement direction of the subject's eye can be specified from the scan result itself. Thereby, it becomes possible to acquire the data of the anterior segment accurately in consideration of the movement direction of the subject's eye, without the error effect due to the deviation between the acquiring timing of the images and the scan timing.

Further, in the ophthalmologic apparatus according to the embodiments, the controller may control the optical scanner to start radial scan in which a plurality of scans including the scan in the intersecting direction are performed radially around a scan center position (C), when the scan center position substantially coincides with a reference position (pupil center position) within the characteristic region in a plane (xy plane) intersecting the traveling direction.

According to such a configuration, the positional displacement of the scan position can be specified from the scan result itself. Thereby, even when the subject's eye moves due to the involuntary eye movement, the line-of-sight deviation, or the like during performing radial scan, it becomes possible to acquire the data of the anterior segment accurately.

Further, in the ophthalmologic apparatus according to the embodiments, the analyzer may include a property distribution calculator (1416) that obtains a distribution of property information of the anterior segment by means of a detection result of the interference light in which positional displacement with respect to the reference position is corrected based on the movement amount and the movement direction.

According to such a configuration, even when the subject's eye moves due to the involuntary eye movement, the line-of-sight deviation, or the like during scanning, it becomes possible to obtain the property information of the anterior segment accurately.

Further, in the ophthalmologic apparatus according to the embodiments, the property information may include at least one of corneal shape information, corneal thickness information, and anterior chamber depth information.

According to such a configuration, even when the subject's eye moves due to the involuntary eye movement, the line-of-sight deviation, or the like during scanning, it becomes possible to obtain the corneal shape information, the corneal thickness information, the anterior chamber depth information, or the like accurately.

Further, the ophthalmologic apparatus according to the embodiments further may include a movement mechanism (first drive mechanism 80A, second drive mechanism 80B) that moves the subject's eye and the interference optical system relative to each other, wherein the reference position may be a registration reference position of the interference optical system with respect to the subject's eye.

According to such a configuration, the ophthalmologic apparatus capable of accurately acquiring the data of the anterior segment of the subject's eye in consideration of the positional displacement of the scan position with respect to the registration reference position can be provided.

Further, in the ophthalmologic apparatus according to the embodiments, the reference position may be a pupil center position, a pupil barycentric position, a corneal center position, a corneal apex position, or a center position of the subject's eye.

According to such a configuration, the ophthalmologic apparatus capable of accurately acquiring the data of the anterior segment of the subject's eye in consideration of the positional displacement of the scan position with respect to the pupil center position, the pupil barycentric position, the corneal center position, the corneal apex position, or the center position of the subject's eye can be provided.

Further, in the ophthalmologic apparatus according to the embodiments, the reference value may be a value corresponding to a pupil diameter, an iris outer diameter, or a distance between corner angles obtained by performing scan which passes through the reference position.

According to such a configuration, the movement amount or the movement direction of the subject's eye can be specified by using a known method for specifying the pupil diameter, the iris outer diameter, or the distance between corner angles.

Further, the ophthalmologic apparatus according to the embodiments further may include an anterior segment imaging system (anterior segment cameras 60) for imaging the anterior segment, wherein the analyzer may include a first specifying unit (characteristic region analyzer 1412) that specifies the reference value in the characteristic region by analyzing an anterior segment image acquired by using the anterior segment imaging system.

According to such a configuration, the ophthalmologic apparatus capable of specifying the reference value of the characteristic region in the anterior segment and accurately acquiring the data of the anterior segment of the subject's eye in consideration of the movement amount or the movement direction of the subject's eye based on the specified reference value can be provided.

Further, the ophthalmologic apparatus according to the embodiments further may include an image forming unit (13) that forms a tomographic image of the anterior segment based on the detection result of the interference light, wherein the analyzer may include a second specifying unit (movement amount specifying unit 1413, movement direction specifying unit 1414) that specifies the scan length by analyzing the tomographic image.

According to such a configuration, the scan length can be specified by analyzing the tomographic image. Thereby, it becomes possible to accurately acquire the data of the anterior segment of the subject's eye in consideration of the movement amount or the movement direction of the subject's eye based on the cross-sectional shape of the anterior segment.

Further, a method of controlling an ophthalmologic apparatus (1) according to the embodiments scans an anterior segment (Ea) of a subject's eye (E) by using optical coherence tomography. The method of controlling the ophthalmologic apparatus includes a projection step, a control step, an interference light detection step, and a movement amount specifying step. The projection step splits light from a light source into measurement light and reference light and projects the measurement light onto a subject's eye via an optical scanner (40). The control step controls the optical scanner so as to perform scan by the measurement light in an intersecting direction (B scan direction) which intersects a traveling direction of the measurement light incident on the anterior segment. The interference light detection step detects interference light generated from returning light of the measurement light from the subject's eye and the reference light. The movement amount specifying step specifies a scan length based on a detection result of the interference light corresponding to the scan, the scan length being a length of a scan range in the intersecting direction within a characteristic region in the anterior segment, and specifies a movement amount of the subject's eye based on a reference value of the characteristic region and the scan length.

According to such a configuration, while deflecting the measurement light in the intersecting direction which intersects the traveling direction, the scan length in the intersecting direction within the characteristic region of the anterior segment can be specified. Thereby the movement amount of the subject's eye corresponding to the scan length with reference to the reference value of the characteristic region can be specified. As a result, the movement amount of the subject's eye can be specified from the scan result itself. Therefore, even when the subject's eye moves due to the involuntary eye movement, the line-of-sight deviation, or the like during scanning, it becomes possible to acquire the data of the anterior segment accurately in consideration of the movement amount of the subject's eye, without the error effect due to the deviation between the acquiring timing of the images and the scan timing.

Further, the method of controlling the ophthalmologic apparatus according to the embodiments may include a movement direction specifying step that specifies a movement direction of the subject's eye based on a position of the scan range within the characteristic region in an entire scan range of the scan.

According to such a configuration, the movement direction of the subject's eye can be specified from the scan result itself. Thereby, it becomes possible to acquire the data of the anterior segment accurately in consideration of the movement direction of the subject's eye, without the error effect due to the deviation between the acquiring timing of the images and the scan timing.

Further, in the method of controlling the ophthalmologic apparatus according to the embodiments, in the control step, radial scan in which a plurality of scans including the scan in the intersecting direction are performed radially around a scan center position may be started, when the scan center position substantially coincides with a reference position within the characteristic region in a plane intersecting the traveling direction.

According to such a configuration, the positional displacement of the scan position can be specified from the scan result itself. Thereby, even when the subject's eye moves due to the involuntary eye movement, the line-of-sight deviation, or the like during performing radial scan, it becomes possible to acquire the data of the anterior segment accurately.

Computer programs for realizing the above embodiments can be stored in any kind of recording medium that can be read by a computer. As this recording medium, for example, a semiconductor memory, an optical disk, a magneto-optic disk (CD-ROM, DVD-RAM, DVD-ROM, MO, and so on), and a magnetic storage (a hard disk, a floppy Disk™, ZIP, and so on) can be used.

The program may be sent/received through a network such as the Internet or LAN.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
an optical scanner;
an interference optical system that splits light from a light source into measurement light and reference light, projects the measurement light onto a subject's eye via the optical scanner, and detects interference light generated from returning light of the measurement light from the subject's eye and the reference light;
a controller that controls the optical scanner so as to perform a scan by the measurement light in an intersecting direction which intersects a traveling direction of the measurement light; and
an analyzer that specifies a scan length based on a detection result of the interference light corresponding to the scan, the detection result being acquired by the interference optical system, the scan length being a length of a scan range in the intersecting direction within a characteristic region in an anterior segment of the subject's eye, and specifies a movement amount of the subject's eye based on a reference value of the characteristic region and the scan length,
wherein the scan length is the length of the scan range in which a scan line passes through the characteristic region in the anterior segment of the subject's eye in the intersecting direction that intersects the traveling direction of the measurement light, and
the analyzer specifies the movement amount of the subject's eye based on a ratio of the scan length to the reference value.

2. The ophthalmologic apparatus of claim 1, wherein
the analyzer specifies a movement direction of the subject's eye based on a position of the scan range within the characteristic region in an entire scan range of the scan.

3. The ophthalmologic apparatus of claim 2, wherein
the controller controls the optical scanner to start a radial scan in which a plurality of scans including the scan in the intersecting direction are performed radially around a scan center position, when the scan center position substantially coincides with a reference position within the characteristic region in a plane intersecting the traveling direction.

4. The ophthalmologic apparatus of claim 3, wherein
the analyzer includes a property distribution calculator that obtains a distribution of property information of the anterior segment by means of a detection result of the interference light in which positional displacement with respect to the reference position is corrected based on the movement amount and the movement direction.

5. The ophthalmologic apparatus of claim 4, wherein
the property information includes at least one of corneal shape information, corneal thickness information, and anterior chamber depth information.

6. The ophthalmologic apparatus of claim 3, further comprising:
a movement mechanism that moves the subject's eye and the interference optical system relative to each other, wherein
the reference position is a registration reference position of the interference optical system with respect to the subject's eye.

7. The ophthalmologic apparatus of claim 3, wherein
the reference position is a pupil center position, a pupil barycentric position, a corneal center position, a corneal apex position, or a center position of the subject's eye.

8. The ophthalmologic apparatus of claim 3, wherein
the reference value is a value corresponding to a pupil diameter, an iris outer diameter, or a distance between corner angles obtained by performing scan which passes through the reference position.

9. The ophthalmologic apparatus of claim 1, further comprising:
an anterior segment imaging system for imaging the anterior segment, wherein
the analyzer comprises a first specifying unit that specifies the reference value in the characteristic region by analyzing an anterior segment image acquired by using the anterior segment imaging system.

10. The ophthalmologic apparatus of claim 1, further comprising:
an image forming unit that forms a tomographic image of the anterior segment based on the detection result of the interference light, wherein
the analyzer includes a second specifying unit that specifies the scan length by analyzing the tomographic image.

11. A method of controlling an ophthalmologic apparatus that scans an anterior segment of a subject's eye by using optical coherence tomography, the method comprising:
a projection step that splits light from a light source into measurement light and reference light and projects the measurement light onto a subject's eye via an optical scanner;
a control step that controls the optical scanner so as to perform a scan by the measurement light in an intersecting direction which intersects a traveling direction of the measurement light incident on the anterior segment;
an interference light detection step that detects interference light generated from returning light of the measurement light from the subject's eye and the reference light; and
a movement amount specifying step that specifies a scan length based on a detection result of the interference light corresponding to the scan, the scan length being a length of a scan range in the intersecting direction within a characteristic region in the anterior segment, and specifies a movement amount of the subject's eye based on a reference value of the characteristic region and the scan length,
wherein the scan length is the length of the scan range in which a scan line passes through the characteristic region in the anterior segment of the subject's eye in the intersecting direction that intersects the traveling direction of the measurement light, and
the movement amount specifying step specifies the movement amount of the subject's eye based on a ratio of the scan length to the reference value.

12. The method of controlling the ophthalmologic apparatus of claim 11, further comprising:
a movement direction specifying step that specifies a movement direction of the subject's eye based on a position of the scan range within the characteristic region in an entire scan range of the scan.

13. The method of controlling the ophthalmologic apparatus of claim 11, wherein
in the control step, a radial scan in which a plurality of scans including the scan in the intersecting direction are performed radially around a scan center position is started, when the scan center position substantially coincides with a reference position within the characteristic region in a plane intersecting the traveling direction.

\* \* \* \* \*